(12) United States Patent
Girouard et al.

(10) Patent No.: US 7,493,162 B2
(45) Date of Patent: Feb. 17, 2009

(54) PULMONARY VEIN STENT FOR TREATING ATRIAL FIBRILLATION

(75) Inventors: Steven D. Girouard, Woodbury, MN (US); Bruce H. KenKnight, Maple Grove, MN (US); David S. Wood, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 405 days.

(21) Appl. No.: 10/160,269

(22) Filed: May 31, 2002

(65) Prior Publication Data

US 2003/0069606 A1   Apr. 10, 2003

Related U.S. Application Data

(60) Provisional application No. 60/298,741, filed on Jun. 15, 2001.

(51) Int. Cl.
*A61N 1/00* (2006.01)
(52) U.S. Cl. .......................................................... 607/5
(58) Field of Classification Search .................. 607/5, 607/115, 116, 119, 120, 154, 2; 600/122, 600/2, 3, 439; 606/34
See application file for complete search history.

(56) References Cited

U.S. PATENT DOCUMENTS

| | | | | |
|---|---|---|---|---|
| 3,692,027 A | 9/1972 | Ellinwood, Jr. | ............. | 128/260 |
| 4,003,379 A | 1/1977 | Ellinwood, Jr. | ............. | 128/260 |
| 4,146,029 A | 3/1979 | Ellinwood, Jr. | ............. | 128/260 |
| 4,281,664 A | 8/1981 | Duggan | ............. | 128/696 |
| 4,299,220 A | 11/1981 | Dorma | ............. | 128/260 |
| 4,544,371 A | 10/1985 | Dormandy, Jr. et al. | ..... | 604/891 |
| 4,556,063 A | 12/1985 | Thompson et al. | ..... | 128/419 PT |
| 4,686,987 A | 8/1987 | Salo et al. | ............. | 128/419 PG |
| 4,800,882 A | 1/1989 | Gianturco | | |

(Continued)

FOREIGN PATENT DOCUMENTS

EP  0054138  10/1981

(Continued)

OTHER PUBLICATIONS

"Initation of atrial fibrillation by ectopic beats originating from the superior vena cava: electrophysiological characteristics and results of radiofrquency ablation," Tsai et al., Circulation, vol. 102, Iss. 1, p. 67 (Jul. 2000) (Abstract).*

(Continued)

*Primary Examiner*—George Manuel
(74) *Attorney, Agent, or Firm*—Schwegman, Lundberg & Woessner, P.A.

(57) ABSTRACT

An apparatus and method for treating atrial fibrillation is described that uses a vascular stent deployed within the pulmonary veins of the left atrium. The stent may be used alone or in combination with chemical, thermal, electrical, or radioactive energy sources to ablate myocardial tissue residing in the pulmonary veins. The targeted myocardial tissue in the pulmonary veins will have been identified as the source of initiation and/or sustenance of atrial fibrillation. Ablation therapy using the pulmonary venous stent stops discharges from ectopic foci in the vein or alternatively stops impulses from reaching the left atrium. The deployed stent can then be left in place to prevent stenosis of the vein.

12 Claims, 2 Drawing Sheets

U.S. PATENT DOCUMENTS

| | | | |
|---|---|---|---|
| 4,871,351 A | 10/1989 | Feingold | 604/66 |
| 4,897,987 A | 2/1990 | Spalla | 56/16.7 |
| 4,907,336 A | 3/1990 | Gianturco | |
| 4,936,281 A | 6/1990 | Stasz | |
| 4,944,299 A | 7/1990 | Silvian | 128/419 PG |
| 4,987,897 A | 1/1991 | Funke | 128/419 PG |
| 4,994,033 A | 2/1991 | Shockey et al. | |
| 5,040,533 A | 8/1991 | Fearnot | 128/419 PG |
| 5,041,107 A | 8/1991 | Heil, Jr. | 604/891.1 |
| 5,042,497 A | 8/1991 | Shapland | 128/696 |
| 5,058,581 A | 10/1991 | Silvian | 128/419 PG |
| 5,078,736 A | 1/1992 | Behl | |
| 5,087,243 A | 2/1992 | Avitall | 604/20 |
| 5,127,404 A | 7/1992 | Wyborny et al. | 128/419 P |
| 5,178,618 A * | 1/1993 | Kandarpa | 606/28 |
| 5,190,035 A | 3/1993 | Salo et al. | 128/419 |
| 5,220,917 A | 6/1993 | Cammilli et al. | 128/419 D |
| 5,269,301 A | 12/1993 | Cohen | 607/6 |
| 5,284,136 A | 2/1994 | Hauck et al. | 607/24 |
| 5,292,321 A | 3/1994 | Lee | |
| 5,305,745 A | 4/1994 | Zacouto | 128/637 |
| 5,342,408 A | 8/1994 | deCoriolis et al. | 607/32 |
| 5,353,800 A | 10/1994 | Pohndorf et al. | 128/673 |
| 5,368,028 A | 11/1994 | Palti | 128/635 |
| 5,404,877 A | 4/1995 | Nolan et al. | 128/671 |
| 5,411,466 A * | 5/1995 | Hess | 600/3 |
| 5,416,695 A | 5/1995 | Stutman et al. | 364/413.02 |
| 5,456,692 A | 10/1995 | Smith, Jr. et al. | 607/31 |
| 5,460,605 A | 10/1995 | Tuttle et al. | 604/67 |
| 5,496,360 A | 3/1996 | Hoffmann et al. | 607/120 |
| 5,499,971 A | 3/1996 | Shapland et al. | 604/53 |
| 5,551,953 A | 9/1996 | Lattin et al. | 604/20 |
| 5,556,421 A | 9/1996 | Prutchi et al. | 607/36 |
| 5,562,713 A | 10/1996 | Silvian | 607/32 |
| 5,579,876 A | 12/1996 | Adrian et al. | 188/322.17 |
| 5,586,556 A | 12/1996 | Spivey et al. | 128/697 |
| 5,607,418 A | 3/1997 | Arzbaecher | 604/891.1 |
| 5,607,463 A | 3/1997 | Schwartz et al. | |
| 5,634,899 A | 6/1997 | Shapland et al. | 604/51 |
| 5,637,113 A | 6/1997 | Tartaglia et al. | |
| 5,662,689 A | 9/1997 | Elsberry et al. | 607/5 |
| 5,690,682 A | 11/1997 | Buscemi et al. | 607/3 |
| 5,693,075 A | 12/1997 | Plicchi et al. | 607/17 |
| 5,693,085 A | 12/1997 | Buirge et al. | |
| 5,720,770 A | 2/1998 | Nappholz et al. | 607/30 |
| 5,730,125 A | 3/1998 | Prutchi et al. | 128/637 |
| 5,766,192 A | 6/1998 | Zacca | |
| 5,775,338 A | 7/1998 | Hastings | |
| 5,800,498 A | 9/1998 | Obino et al. | 607/123 |
| 5,814,089 A | 9/1998 | Stokes et al. | |
| 5,817,131 A | 10/1998 | Elsberry et al. | 607/5 |
| 5,833,603 A | 11/1998 | Kovacs et al. | 600/317 |
| 5,836,935 A | 11/1998 | Ashton et al. | 604/891.1 |
| 5,846,218 A | 12/1998 | Brisken et al. | |
| 5,876,433 A | 3/1999 | Lunn | |
| 5,893,881 A | 4/1999 | Elsberry et al. | 607/5 |
| 5,899,917 A | 5/1999 | Edwards et al. | |
| 5,899,928 A | 5/1999 | Sholder et al. | 607/27 |
| 5,906,636 A | 5/1999 | Casscells, III et al. | |
| 5,921,954 A | 7/1999 | Mohr, Jr. et al. | |
| 5,925,066 A | 7/1999 | Kroll et al. | 607/3 |
| 5,944,710 A | 8/1999 | Dev et al. | |
| 5,949,659 A | 9/1999 | Lesche | 363/16 |
| 5,954,761 A | 9/1999 | Machek et al. | 607/126 |
| 5,967,986 A | 10/1999 | Cimochowski et al. | 600/454 |
| 5,972,029 A | 10/1999 | Fuisz | |
| 5,980,563 A * | 11/1999 | Tu et al. | 607/113 |
| 5,980,566 A | 11/1999 | Alt et al. | |
| 5,991,668 A | 11/1999 | Leinders et al. | 607/125 |
| 6,004,269 A * | 12/1999 | Crowley et al. | 600/439 |
| 6,016,447 A | 1/2000 | Juran et al. | 607/27 |
| 6,016,448 A | 1/2000 | Busacker et al. | 607/29 |
| 6,024,740 A * | 2/2000 | Lesh et al. | 606/34 |
| 6,053,913 A | 4/2000 | Tu et al. | |
| 6,102,908 A * | 8/2000 | Tu et al. | 606/41 |
| 6,115,636 A | 9/2000 | Ryan | 607/60 |
| 6,140,740 A | 10/2000 | Porat et al. | 310/322 |
| 6,141,588 A | 10/2000 | Cox et al. | |
| 6,154,675 A | 11/2000 | Juran et al. | 607/29 |
| 6,168,801 B1 | 1/2001 | Heil, Jr. et al. | 424/426 |
| 6,179,789 B1 * | 1/2001 | Tu et al. | 600/585 |
| 6,179,824 B1 | 1/2001 | Eggers et al. | |
| 6,198,394 B1 | 3/2001 | Jacobsen et al. | 340/573.1 |
| 6,200,265 B1 | 3/2001 | Walsh et al. | 600/300 |
| 6,206,914 B1 | 3/2001 | Soykan et al. | 623/1.42 |
| 6,213,942 B1 | 4/2001 | Flach et al. | 600/300 |
| 6,231,516 B1 | 5/2001 | Keilman et al. | 600/485 |
| 6,237,398 B1 | 5/2001 | Porat et al. | 73/54.09 |
| 6,251,109 B1 * | 6/2001 | Hassett et al. | 606/45 |
| 6,254,573 B1 | 7/2001 | Haim et al. | 604/157 |
| 6,272,377 B1 | 8/2001 | Sweeney et al. | |
| 6,277,078 B1 | 8/2001 | Porat et al. | 600/486 |
| 6,298,272 B1 | 10/2001 | Peterfeso et al. | 607/120 |
| 6,309,370 B1 | 10/2001 | Haim et al. | 604/66 |
| 6,317,615 B1 | 11/2001 | KenKnight et al. | 600/372 |
| 6,358,202 B1 | 3/2002 | Arent | 600/300 |
| 6,361,522 B1 | 3/2002 | Scheiner et al. | 604/67 |
| 6,361,780 B1 | 3/2002 | Ley et al. | 424/400 |
| 6,424,847 B1 | 7/2002 | Mastrototaro et al. | 600/316 |
| 6,442,413 B1 | 8/2002 | Silver | |
| 6,443,949 B2 | 9/2002 | Altman | 606/41 |
| 6,453,195 B1 | 9/2002 | Thompson | 607/3 |
| 6,459,917 B1 | 10/2002 | Gowda et al. | 600/345 |
| 6,501,983 B1 | 12/2002 | Natarajan et al. | 600/517 |
| 6,511,477 B2 | 1/2003 | Altman et al. | 606/41 |
| 6,514,249 B1 | 2/2003 | Maguire et al. | |
| 6,518,245 B1 | 2/2003 | Anderson et al. | 514/14 |
| 6,519,488 B2 | 2/2003 | KenKnight et al. | 600/372 |
| 6,542,781 B1 * | 4/2003 | Koblish et al. | 607/122 |
| 6,632,223 B1 * | 10/2003 | Keane | 606/41 |
| 6,645,145 B1 | 11/2003 | Dreschel et al. | |
| 6,648,881 B2 | 11/2003 | KenKnight et al. | |
| 6,662,045 B2 | 12/2003 | Zheng et al. | |
| 6,716,242 B1 * | 4/2004 | Altman | 623/1.42 |
| 6,939,345 B2 | 9/2005 | KenKnight et al. | |
| 6,955,640 B2 * | 10/2005 | Sanders et al. | 600/3 |
| 2001/0000802 A1 | 5/2001 | Soykan et al. | 623/1.13 |
| 2002/0026228 A1 | 2/2002 | Schauerte | |
| 2003/0004403 A1 | 1/2003 | Drinan et al. | 600/301 |
| 2003/0018362 A1 | 1/2003 | Fellows | |
| 2003/0153952 A1 | 8/2003 | Auricchio et al. | |
| 2003/0158584 A1 | 8/2003 | Cates et al. | |
| 2004/0093034 A1 | 5/2004 | Girouard et al. | |

FOREIGN PATENT DOCUMENTS

| | | |
|---|---|---|
| EP | 1050265 | 11/2000 |
| WO | WO-97/33513 | 3/1997 |

OTHER PUBLICATIONS

"Local delivery of chemotherapy: a supplement to existing cancer treatments A case for surgical pastes and coated stents," Hunter et al., Advanced Drug Delivery Reviews 26, pp. 199-207 (1997).*

Definition of "brachytherapy" from dictionary.com.*

U.S. Appl. No. 10/123,897.*

Brunner, Friedrich, et al., "Attenuation of myocardial ischemia/reperfusion injury in mice with myocyte-specific overexpression of endothelial nitric oxide synthase", *CArdiovascular Research*, 57, (2003),55-62.

Flogel, Ulrich, et al., "Myoglobin: A scanvenger of bioactive NO", *PNAS*, vol. 98, No. 2, (Jan. 16, 2001),735-740.

Gewaltig, Michael T., et al., "Vasoprotection ny nitric oxide: mechanisms and therapeutic potential", *Cardiovascular Research*, 55, (Feb. 14, 2002),250-260.

Li, Qianghong, et al., "Gene Therapy With Inducible Nitric Oxide Synthase Protects Against Myocardial Infarction via a Cyclooxygenase-2-Dependent Mechanism", *Circulation Research*, 92, (2003),741-748.

Paolocci, N., et al., "Positive inotropic and lusitropic effects of HNO/NO- in failing hearts: independence from beta-adrenergic signaling", *Proc. Natl. Acad. Sci. USA*, 100(9), 2003,4978-80.

Salloum, Fadi, et al., "Sildenafil Induces Delayed Preconditioning Through Inducible Nitric Oxide Synthase-Dependent Pathway in Mouse Heart", *Circulation Research*, 92, (Apr. 4, 2003),595-597.

Wunderlich, Carsten, et al., "Acute Inhibition of Myoglobin Impairs Contractility and Energy State of iNOS-Overexpressing Hearts", *Circulation Research*, 92, (2003),1352-1358.

Burns, Brent E., "Fabrication Technology for a Chronic In-Vivo Pressure Sensor", *1984 International Electron Devices Meeting Technical Digest*, (1984),210-212.

Carr, William N., "Integrated Pressure Sensor With Remote Power Source and Remote Readout", *The 8th International Conference on Solid-State Sensors and Actuators and Eurosensors IX, Digest of Technical Papers*, Stockholm, Sweden, (Jun. 25-29, 1995),624-627.

Chau, Hin-Leung, "An Ultraminiature Solid-State Pressure Sensor for a Cardiovascular Catheter", *IEEE Transactions on Electron Devices*, (Dec. 1988),2355-2362.

Pastore, Joseph M., "Method And Apparatus For Modulating Cellular Metabolism During Post-Ischemia Or Heart Failure", *U.S. Appl. No. 10/645,823, Filed Aug. 21, 2003*, 46 pages.

Spiegel, Egbert, "A CMOS Sensor and Signal Conversion Chip for Monitoring Arterial Blood Pressure and Temperature", *IEEE International Solid-State Circuits Conference,*, (Feb. 20, 1992), 126-127.

Ziaie, Babak, "A Single-Channel Implantable Microstimulator for Functional Neuromuscular Stimulation", *IEEE Transactions on Biomedical Engineering*, 44, (Oct. 1997),909-920.

"U.S. Appl. No. 10/123,897 Non Final Office Action mailed Apr. 12, 2005", 8 pgs.

"U.S. Appl. No. 10/123,897 Notice of Allowance mailed Oct. 5, 2005", 9 pgs.

"U.S. Appl. No. 10/123,897 Notice of Allowance mailed Dec. 6, 2006", 7 pgs.

"U.S. Appl. No. 10/123,897 Response filed Jul. 12, 2005 to Non Final Office Action mailed Apr. 12, 2005", 6 pgs.

\* cited by examiner

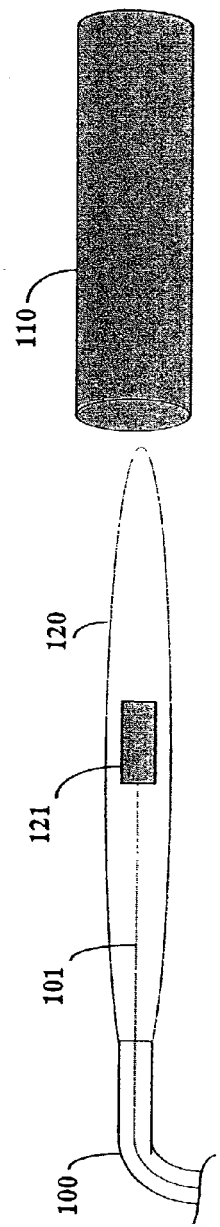
FIG. 2
FIG. 3B
FIG. 3A

PULMONARY VEIN STENT FOR TREATING ATRIAL FIBRILLATION

CROSS-REFERENCE TO RELATED APPLICATION(S)

This application claims the benefit of U.S. Provisional Application No. 60/298,741, filed on Jun. 15, 2001, under 35 U.S.C. 119(e).

FIELD OF THE INVENTION

This invention pertains to methods for treating atrial tachyarrhythmias such as atrial fibrillation. In particular, the invention relates to an apparatus and method for treating atrial fibrillation using vascular stents in the great veins of the atria.

BACKGROUND

Fibrillation refers to a condition in which muscle fibrils enter a state of extremely rapid, small-scale contractions that do not coordinate to affect contraction of the muscle as a whole. When this occurs in the left ventricle, the heart chamber responsible for pumping blood into the arterial vasculature, it is serious and rapidly fatal. When it occurs in the musculature of the atria, it is less immediately serious and not necessarily fatal. It is still important to treat atrial fibrillation, however, for several reasons. First, atrial fibrillation is associated with a loss of atrio-ventricular synchrony which can be hemodynamically compromising and cause such symptoms as dyspnea, fatigue, vertigo, and angina. Atrial fibrillation can also predispose to stroke or cerebral vascular accidents resulting from emboli forming in the left atrium. Although drug therapy, in-hospital cardioversion, and implantable cardioverter/defibrillators are acceptable treatment modalities for atrial fibrillation, a curative approach such as ablation therapy offers a number of advantages to certain patients, including convenience and greater efficacy.

Electrical ablation therapy treats cardiac arrhythmias by destroying myocardial tissue involved in the initiation or maintenance of the tachyarrhythmia. Ablation is most often accomplished by delivering radiofrequency electrical energy to a catheter electrode that has been placed next to the tissue to be destroyed. One way that the technique has been employed in order to treat atrial fibrillation is to identify ectopic sites or reentrant pathways electrophysiologically by mapping the electrical activation of the atria. Once candidate sites for ablation are identified they are ablated by the application of radiofrequency energy. Recent evidence has shown that a high percentage of paroxysms of atrial fibrillation are initiated by trains of rapid discharges originating from the pulmonary veins of the left atrium. Accordingly, catheter techniques have been developed for ablating these sites with radiofrequency energy applied from within the pulmonary veins, but electrophysiological mapping of such sites is difficult. Alternatively, another ablation technique involves the production of a circumferential ablation lesion within a pulmonary vein in order to block the conduction pathway from the vein to the left atrium. An effective circumferential lesion must be completely circular, however, and this means that the ablation device must be precisely centered within the vein or ostium, which may be difficult to accomplish. Furthermore, a common complication of this procedure is pulmonary venous stenosis resulting from scarring within the pulmonary vein with variable clinical consequences.

SUMMARY OF THE INVENTION

An objective of the present invention is to provide an improved apparatus and method for pulmonary vein ablation in order to treat atrial fibrillation. In accordance with the invention, a stent catheter having a stent mounted thereon is introduced into the left atrium of a patient. The stent is deployed by expansion of the stent within a pulmonary vein or ostium of the vein. The stent expansion may be performed with a balloon at the distal end of the stent catheter. Tissue surrounding the deployed stent is then ablated to stop discharges from ectopic foci in the vein from reaching the left atrium. The ablation lesions in the tissue surrounding the stent may be selectively produced so as to destroy one or more ectopic foci, or a circumferential lesion may be produced that interrupts a conduction pathway between the vein and the left atrium. Following the procedure the stent remains in the target vein as a chronic implant. In one embodiment, ablation of surrounding tissue occurs via a tissue reaction with the surface of the stent resulting in fibrosis and loss of myocardial tissue in the region surrounding the stent body. In another embodiment, energy is transmitted into the surrounding tissue by means of a catheter making contact with the stent in order to produce a circumferential ablation of tissue in contact with the stent surface. Such energy may be electrical energy transmitted by a catheter making contact with the stent that causes heating and necrosis of the myocardial tissue surrounding the stent. Alternatively, tissue may be ablated by thermal energy using a cryogenic probe mounted on a catheter that contacts the stent. In another embodiment radiation energy emitted by a radioactive isotope may be used to affect myocardial tissue necrosis.

BRIEF DESCRIPTION OF THE DRAWINGS

FIG. 2 shows a stent catheter with an energy transmission element.

FIGS. 3A-B show examples of stent electrodes.

DETAILED DESCRIPTION OF THE INVENTION

It has been found that the ectopic foci responsible for many episodes of atrial fibrillation are found in the great veins of the atrium known as the pulmonary veins. The pulmonary veins empty into the left atrium, and a myocardial muscle sleeve extends from the left atrium into the proximal segment of the pulmonary veins. The myocytes in these pulmonary vein sleeves, unlike ordinary atrial myocytes, may exhibit spontaneous activity and can thus constitute ectopic sites responsible for initiating and maintaining atrial fibrillation. In order to block the discharges from these myocytes with ablation therapy, either the myocytes themselves are destroyed or an ablation lesion is made that destroys excitable tissue in the pathway leading from the myocytes to the left atrium.

Figure 1A:
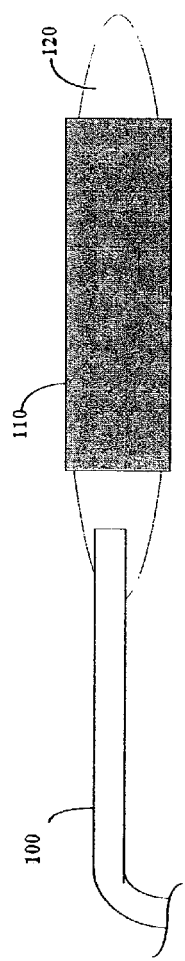
FIGS. 1A-B depict a stent catheter with a stent fixed at one end.
Figure 1B:
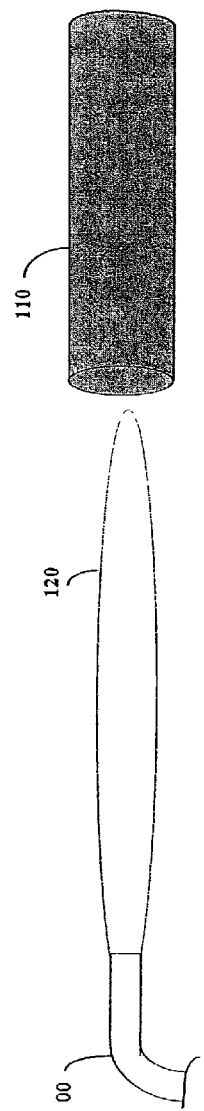

Shown in FIG. 1A is a depiction of a stent catheter 100 having a balloon 120 at its distal end. Fitted around the balloon 120 is a vascular stent 110, which is a tubular structure made of metal or synthetic material capable of being deployed in a pulmonary vein similar to the way arterial stents are deployed in peripheral or coronary arteries. Pressurized fluid applied to the proximal end of the catheter passes through a lumen within the catheter and inflates the balloon 120. Inflating the balloon 120 expands the stent 110 against the walls of a blood vessel and thereby deploys the stent in a fixed position within the vessel. Once the stent is deployed, the balloon is deflated and the catheter pulled back to leave the stent in place as shown in FIG. 1B. In another embodiment, a self-expanding stent delivered by a catheter is employed.

The stent catheter 100 with the stent 110 fixed thereon may be positioned in a pulmonary vein using an over the wire catheterization technique in which a radio-opaque catheter, or guidewire over which the catheter slides, is passed into a patient's vascular system under fluoroscopic guidance. Vascular access is obtained by puncturing a vessel and seating a hemostatic valve within the puncture wound. The stent catheter is then passed into the patient's vascular system through the valve. In one approach, the catheter is introduced into a peripheral vein and then advanced through the vena cava and into the right atrium. From there, the catheter is positioned against the fossa ovalis in the atrial septum, and a needle or trochar is advanced distally through a lumen of the stent catheter and out the distal end to puncture the fossa ovalis. The catheter is then passed through atrial septum to reach the left atrium and the pulmonary veins. In another approach, the catheter is advanced into the left atrium from the arterial system by accessing a peripheral artery and advancing the catheter into the aorta, around the aortic arch, into the left ventricle, and then into the left atrium through the mitral valve. With either approach, after reaching the left atrium, the distal end of the stent catheter 100 is advanced into a selected pulmonary vein to position the stent 110 within either the vein or the ostium of the vein where the conduction block is to be formed.

The stent 110 is deployed by expanding the stent within the vein by, for example, inflating balloon 120 over which the stent 110 is fitted. Tissue surrounding the deployed stent is then ablated so as to stop discharges from ectopic foci in the vein from reaching the left atrium. The ablation lesions in the tissue surrounding the stent may be selectively produced so as to destroy one or more ectopic foci, or a circumferential lesion may be produced that interrupts a conduction pathway between the vein and the left atrium. After the ablation lesion has been produced, the stent is typically left in place in order to prevent stenosis of the vein as a result of fibrosis and scarring.

In one embodiment, the ablation lesion is produced by a tissue reaction response to the presence of the stent itself that produces a necrotic or fibrotic reaction in the surrounding tissue. The result is a circumferential conduction block around the vein that isolates myocytes in the vein distal to region of fibrosis. In order to promote the tissue reaction responsible for the loss of myocardial tissue, surface coatings may be applied to the stent, or the stent itself may be constructed of a bioincompatible material. Chemotherapeutic agents, for example, may be used as a surface coating to cause cell death and necrosis in tissue contacting the stent surface.

In other embodiments, energy may be applied to the stent in order to cause an ablation lesion. Again, the result is either a circumferential conduction block around the vein which isolates myocytes in the vein distal to the lesion or localized destruction of ectopic foci. Such energy can be applied from the stent catheter or from a separately introduced ablation catheter that contacts the stent. In one embodiment, electrical energy, either direct current or alternating current, is applied to the stent to cause thermal heating of the surrounding tissue. In another embodiment, a cryogenic probe is placed in contact with the stent in order to conduct heat therefrom and ablate a zone of tissue surrounding the stent. In still another embodiment, a radioactive source incorporated into the stent can be used to deliver controlled dose brachytherapy to the surrounding tissue in order to cause cell death and necrosis and thus create an ablation lesion. The radioactive source may be a radioisotope that is either inside the stent material or on the surface of the stent. Alternatively, the radioactive isotope may be introduced for a controlled period of time during the acute procedure and then removed from the patient after a specific does of radiation has been delivered. Using emitted radiation in this manner to create an ablation lesion has a number of advantages over the other methods of applying energy to the stent, including lessened thermal tissue injury to the tissue and a lessened chance of thrombus formation.

FIG. 2 shows an embodiment of a stent catheter 100 in which an energy transmission element 121 is mounted on the balloon 120. The element 121 may be, for example, an electrode, cryogenic element, or radioactive source. In the case where the element 121 is an electrode, the electrode is connected internal to the balloon to a conductor 101 that extends through the lumen of the catheter so that electrical energy can be applied thereto. With either a catheter such as that shown in FIGS. 1A-B or a separate ablation catheter, energy is transmitted from the catheter to the stent which either acts as an electrode or has separate ablation electrodes mounted thereon. In the former case, the stent may be made of any electrically conductive material such as platinum, silver, gold, stainless steel, nitinol, or titanium. FIG. 3A shows an exemplary stent design in which the stent 110 has one or more annular electrodes 111 mounted thereon which effect a circumferential burn when radiofrequency energy is applied to the electrodes. Preferably, the annular electrodes are constructed so as to produce a circumferentially continuous lesion when electrical energy is applied. FIG. 3B shows another embodiment in which the stent 110 has one or more patch electrodes 112 placed at selected locations on the surface of the stent. Such patch electrodes are electrically conductive areas on the stent surface and may be of any desired shape.

Figure 4:
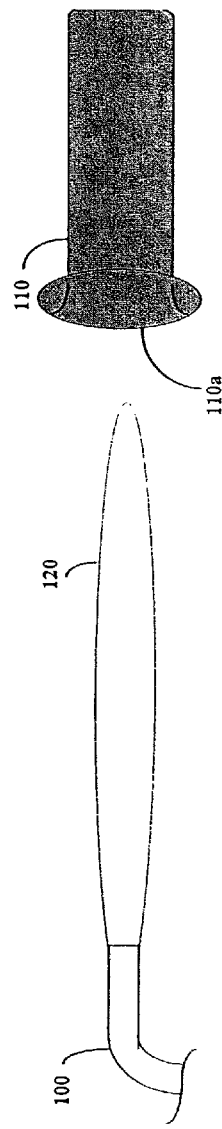
FIG. 4 shows an alternate embodiment of a stent catheter.

In certain patients, ectoptic foci may be found predominantly around the ostia of pulmonary veins within the left atrium. FIG. 4 shows an alternate embodiment of a stent 110 that has a flared end 110a for extending beyond the ostium of a pulmonary vein PV and into the left atrium LA when the stent is deployed. The flared end serves to contact the myocytes which surround the ostium of a pulmonary vein and which may contain ectopic foci. An ablation lesion may then be produced around the flared end of the stent by any of the methods described above, including a tissue reaction with the stent, transmission of electrical energy, cryogenic heat conduction, or brachytherapy.

The method and apparatus for ablating tissue described above has been applied to the pulmonary veins in order to treat atrial fibrillation originating in the left atrium. Although rarer, it is possible for ectopic foci responsible for atrial fibrillation to be located in the inferior or superior vena cava of the right atrium. In this case, the stent catheter can be introduced into the venous system and advanced to the proximal end of either of the vena cava. The ablation method is then performed in the right atrium in the same way as described above for the left atrium.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method, comprising:

introducing a stent catheter having a stent mounted thereon into the left atrium of a patient;

deploying the stent into a pulmonary vein, the superior vena cava, or the inferior vena cava by inflating a balloon at the distal end of the stent catheter to expand the stent within the vein; and, transmitting electrical energy from an electrode mounted on a surface of the balloon to a plurality of electrodes separated by insulation on a surface of the stent to produce a plurality of discrete and unconnected lesions in the tissue surrounding the stent.

2. The method of claim 1 further comprising leaving the stent in the vein after production of the lesions to prevent stenosis.

3. The method of claim 1 wherein the transmitted electrical energy is direct current.

4. The method of claim 1 wherein the transmitted electrical energy is alternating current.

5. The method of claim 1 wherein the plurality of electrodes separated by insulation is a plurality of patch electrodes located on the surface of the stent for producing a plurality of discrete lesions in the tissue surrounding the stent.

6. The method of claim 1 wherein the plurality of electrodes separated by insulation is a plurality of spaced apart annular electrodes located on the surface of the stent for producing a plurality of discrete and unconnected circumferential lesions in the tissue surrounding the stent.

7. The method of claim 1 further comprising:

introducing the catheter into a peripheral vein and then advancing through the vena cava and into the right atrium;

positioning the catheter against the fossa ovalis in the atrial septum and advancing a needle or trochar distally through a lumen of the stent catheter and out the distal end to puncture the fossa ovalis; and, passing the catheter through atrial septum to reach the left atrium.

8. The method of claim 1 further comprising accessing a peripheral artery and advancing the catheter into the aorta, around the aortic arch, into the left ventricle, and then into the left atrium through the mitral valve.

9. An apparatus, comprising:

a stent catheter having a stent mounted thereon;

a balloon at the distal end of the stent catheter to expand the stent within a vessel;

a plurality of electrodes separated by insulation on a surface of the stent;

an electrode mounted on a surface of the balloon for transmitting electrical energy to the plurality of electrodes to thereby produce a plurality of discrete and unconnected lesions in the tissue surrounding the stent.

10. The apparatus of claim 9 wherein the plurality of electrodes separated by insulation is a plurality of patch electrodes located on the surface of the stent for producing a plurality of discrete lesions.

11. The apparatus of claim 9 wherein the plurality of electrodes separated by insulation is a plurality of annular electrodes located on the surface of the stent for producing a plurality of discrete and unconnected circumferential lesions.

12. The apparatus of claim 9 wherein the stent is flared at one end for extending beyond the ostium of a vein when deployed.

* * * * *

UNITED STATES PATENT AND TRADEMARK OFFICE
CERTIFICATE OF CORRECTION

PATENT NO. : 7,493,162 B2 Page 1 of 1
APPLICATION NO. : 10/160269
DATED : February 17, 2009
INVENTOR(S) : Girouard et al.

It is certified that error appears in the above-identified patent and that said Letters Patent is hereby corrected as shown below:

On the Title page, in field (56), under "Other Publications", in column 2, line 1, delete ""Initation" and insert -- "Initiation --, therefor.

On the Title page, in field (56), under "Other Publications", in column 2, line 3, delete "radiofrquency" and insert -- radiofrequency --, therefor.

Signed and Sealed this

Third Day of November, 2009

David J. Kappos
*Director of the United States Patent and Trademark Office*